(12) United States Patent
Bharmi et al.

(10) Patent No.: US 9,199,088 B2
(45) Date of Patent: Dec. 1, 2015

(54) SYSTEM AND METHOD FOR ACCURATELY DETECTING CARDIAC EVENTS USING RETROSPECTIVE CORRELATION

(75) Inventors: Rupinder Bharmi, Canyon Country, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 1921 days.

(21) Appl. No.: 12/264,147

(22) Filed: Nov. 3, 2008

(65) Prior Publication Data

US 2010/0114228 A1    May 6, 2010

(51) Int. Cl.
*A61B 5/04*     (2006.01)
*A61N 1/37*     (2006.01)
*A61B 5/0452*   (2006.01)
*A61B 5/00*     (2006.01)
*A61N 1/362*    (2006.01)
*A61N 1/39*     (2006.01)

(52) U.S. Cl.
CPC .............. *A61N 1/37* (2013.01); *A61B 5/04525* (2013.01); *A61B 5/0002* (2013.01); *A61N 1/3622* (2013.01); *A61N 1/3962* (2013.01)

(58) Field of Classification Search
CPC ..... A61N 1/37; A61N 1/3962; A61N 1/3622; A61B 5/0002; A61B 5/04525
USPC .................................. 600/508–510, 519–521
See application file for complete search history.

(56) References Cited

U.S. PATENT DOCUMENTS

| | | | | |
|---|---|---|---|---|
| 5,984,954 A | * | 11/1999 | Cohen | 600/521 |
| 2004/0243014 A1 | * | 12/2004 | Lee et al. | 600/510 |
| 2006/0247703 A1 | * | 11/2006 | Gutierrez | 607/17 |
| 2008/0140143 A1 | * | 6/2008 | Ettori et al. | 607/14 |

\* cited by examiner

*Primary Examiner* — Michael Kahelin
*Assistant Examiner* — Mallika D Fairchild

(57) ABSTRACT

A system and method enables precise detection of the time of occurrence of a cardiac event of a heart. The method includes the steps of sensing electrical activity of the heart to generate an electrogram signal including the cardiac event, storing the electrogram signal, correlating the electrogram signal with an electrogram template, and identifying the time of occurrence of the cardiac event based upon the correlation.

15 Claims, 4 Drawing Sheets

SYSTEM AND METHOD FOR ACCURATELY DETECTING CARDIAC EVENTS USING RETROSPECTIVE CORRELATION

FIELD OF THE INVENTION

The present invention generally relates to systems and methods for accurately detecting cardiac events and implantable cardiac stimulation devices utilizing such systems and methods. The present invention more particularly relates to such methods, systems, and devices for accurately detecting the beginning of cardiac events by employing retrospective correlation analysis of stored electrograms.

BACKGROUND

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or evoked responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or evoked responses are sensed between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardiac defibrillators (ICD's) are also well known in the art. These devices generally include an arrhythmia detector that detects accelerated arrhythmias, such as tachycardia or fibrillation. When such a tachyarrhythmia is detected, a pulse generator delivers electrical therapy to the patient's heart. A therapy for tachycardia may be anti-tachycardia pacing and a therapy for fibrillation may be a defibrillating shock. Such therapies for both atrial and ventricular tachyarrhythmias are well known.

Implantable cardiac devices find usefulness beyond the provision of the aforementioned therapies. For example, such device may be very useful in the collection data for various types of studies relating to the heart or for monitoring the disease state of a patient.

One parameter commonly important in cardiac data collection is cardiac interval. Cardiac interval determination requires reliable R wave detection. Unfortunately, reliable R wave detection is difficult under many commonly found conditions. Such conditions include varying baseline and changing morphology such as varying R wave amplitude and reduced R/T ratio. The use of fixed threshold R wave detection, commonly found in implantable cardiac devices, makes it difficult to reliably detect the R waves under the noted conditions.

It is very important to be able to precisely detect R waves and accurately determine the starting time of that complex in case of co-morbidity detection. For example, it is known that hypoglycemia can be detected based on monitoring changes in the QT interval observed within an electrocardiogram (ECG), as well as based on observation of dispersion of QT intervals within the ECG. Studies in diabetics have also shown that hypoglycemia can be detected based on observation of a significant lengthening of the QTc interval occurring during spontaneous nocturnal hypoglycemia. R wave detection error is incorporated in the QT interval error as well. All of this leads to poor quality of data for co-morbidity detection and reduces the specificity of the diagnostic. This os true for all co-morbidity detections and any therapy that depends on precise detection of R waves.

SUMMARY

According to one embodiment, a method of precisely detecting the time of occurrence of a cardiac event of a heart comprises the steps of sensing electrical activity of the heart to generate an electrogram signal including the cardiac event, storing the electrogram signal, correlating the electrogram signal with an electrogram template, and identifying the time of occurrence of the cardiac event based upon the correlation.

The step of identifying the time of occurrence of the cardiac event based upon the correlation may include the steps of assigning a point on the electrogram template as a fiducial point and locating a point on the electrogram corresponding to the fiducial point on the electrogram template.

The correlating step is preferably repeated with different offsets between the electrogram signal and the electrogram template. The identifying step may be performed if a highest correlation has a score above a preset score.

The cardiac event may be an R wave. The method may further comprise the steps of detecting the cardiac event with a set detection threshold and establishing a recording window spanning the detected cardiac event. The correlating step may include retrospectively correlating the stored cardiac event with the electrogram template over the recording window.

The sensing step may include generating an electrogram signal and the storing step may include converting the electrogram signal to digital data for storage.

In another embodiment, a system that accurately detects the time of occurrence of a cardiac event of a heart comprises a sensing circuit that senses electrical activity of the heart to generate an electrogram signal including the cardiac event, a memory that stores the electrogram signal, and a processor that correlates the electrogram signal with an electrogram template and identifies the time of occurrence of the cardiac event based upon the correlation.

The processor may be programmed to assign a point on the electrogram template as a fiducial point corresponding to the time of occurrence of the cardiac event and to locate a point on the electrogram corresponding to the fiducial point on the electrogram template.

The processor may be programmed to repeatedly correlate the electrogram signal with the electrogram template with different offsets between the electrogram signal and the electrogram template, and to identify the time of occurrence of the cardiac event based upon the correlation if a highest correlation has a score above a preset score.

The cardiac event may be an R wave. The system may further comprise a detector that detects the cardiac event with a set detection threshold. The processor may be programmed to establish a recording window spanning the detected cardiac event and retrospectively correlate the recorded cardiac event with the electrogram template over the recording window.

The system may further comprise an analog to digital converter that converts the electrogram signal to digital data for storage.

In a further embodiment, an implantable cardiac device includes a system that accurately detects the time of occurrence of a cardiac event of a heart. The device comprises a sensing circuit that senses electrical activity of the heart to generate an electrogram signal including the cardiac event, a memory that stores the electrogram signal, and a processor that correlates the electrogram signal with an electrogram template and identifies the time of occurrence of the cardiac event based upon the correlation.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
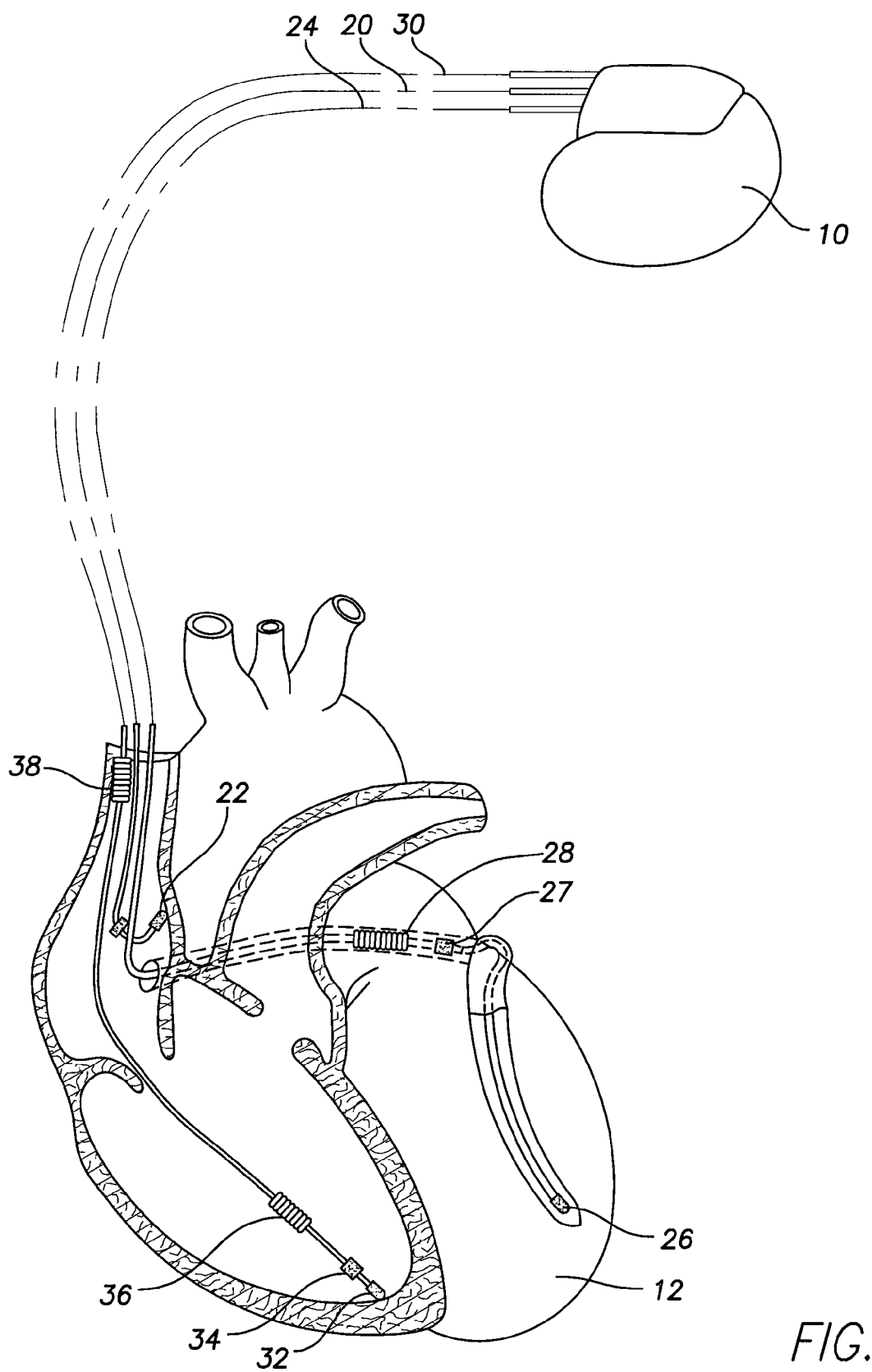
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
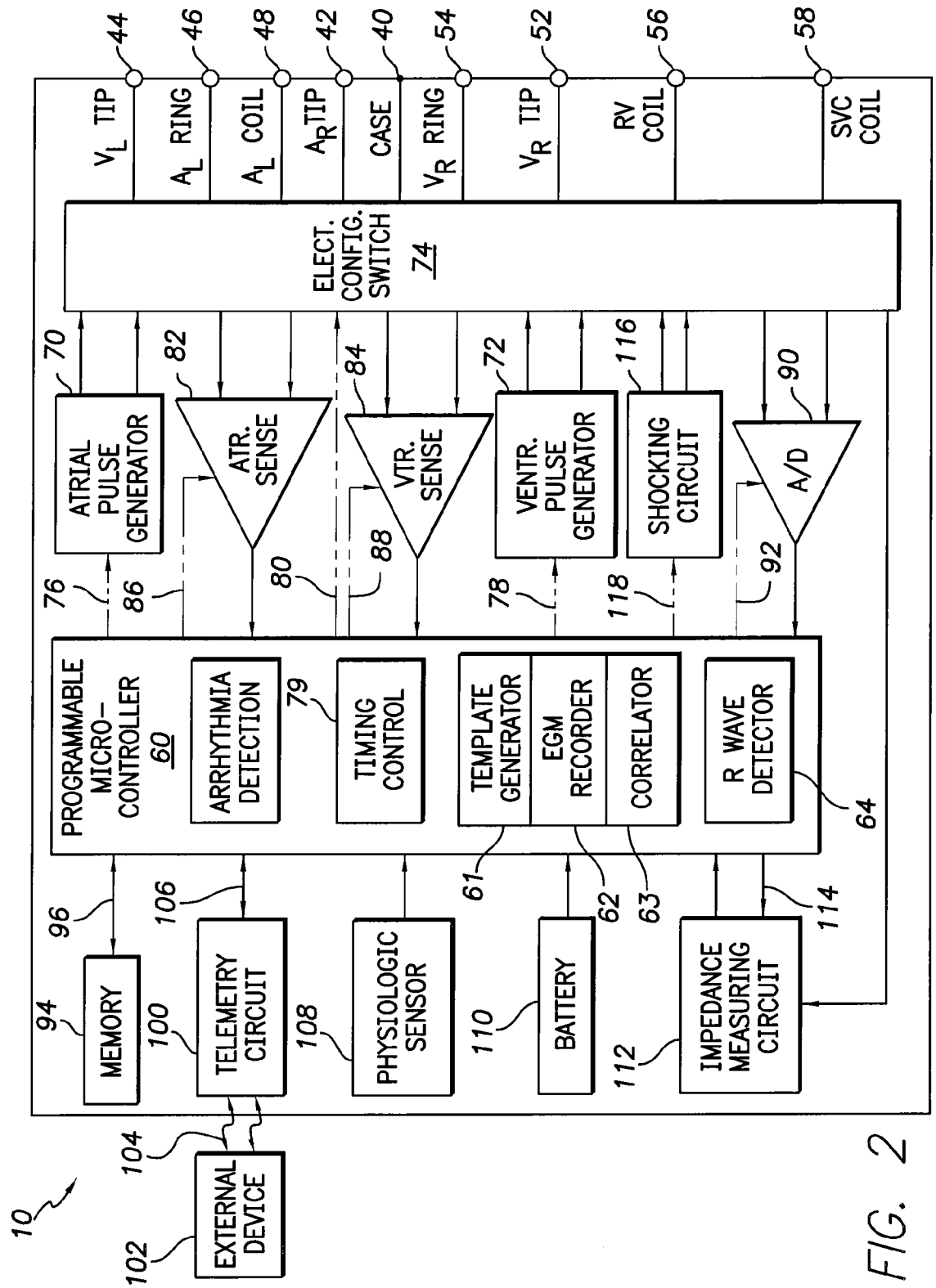
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. Either one of the pulse generators 70 and 72 may be employed for delivering stimulation pulses to or near to the AV node via electrode 22 or electrode 25.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. To that end, the timing control may control the time between individual pulses and the total time in which the pulse are delivered. The timing control 79 may further be used determine ventricular rate, for example.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers.

The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, may receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

The device 10 further includes an arrhythmia detector 75 that utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. The physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With continued reference to FIG. 2, the device further includes a system for precisely detecting the time of occurrence of a cardiac event. While the embodiment described herein is directed towards precisely detecting the time of occurrence of R waves, the invention may be practiced to advantage for precisely timing the occurrence of other types of cardiac events as well including, for example, T waves and P waves, without departing from the present invention.

More particularly, as will be seen hereinafter according to this embodiment, the device establishes a template of the desire cardiac event. This may be accomplished by digitally recording a fixed number of samples (e.g. 32 samples) of a plurality of such events within a recording window, averaging the recorded events and then normalizing the result. A point on the template (herein referred to as a fiducial point) is selected as the starting point of the selected cardiac event.

To accomplish the forgoing, the device includes a template generator 61, and an electrogram (EGM) recorder 62. The template generator 61 may utilize the EGM recorder to set the recording windows and the data acquisition system 90 to perform the EGM recording.

When the device 10 is to record the selected cardiac EGM events, the recording may take place during the recording windows which may be timed off of event detection preformed by an R wave detector 64 used for delivering therapy to the heart. The detector 64 may be a single threshold event detector of the type well known in the art. The test data preferably contains more samples than the template. For example, the test data may include 120 data samples. This permits the correlation window to be shifted by an offset of x samples for each next correlation. In accordance with this embodiment, the window may be shifted five times.

The EGM's are digitized, normalized, and stored in the memory 94, for example. They may then be applied retrospectively to a correlator 63 to correlate each EGM with the previously generated EGM template. More particularly, the recorded EGM windows of the stored EGM's are correlated with the electrogram template which itself may be an EGM template window containing the cardiac event of interest, here, an R wave. The correlation is preferably repeated numerous times with different time offsets between the stored EGM's and the EGM template.

Each correlation results in a correlation score. When a maximum offset is reached, the correlation with the highest score qualifies for use in locating the start time of the cardiac event in that respective EGM. If the highest correlation score is less than a preset score, a mismatch is declared and the EGM data is rejected. However, if the highest correlation score is above the preset score, the offset with the highest correlation score is used to locate the starting point of the cardiac event from the fiducial point on the template.

In accordance with this embodiment, the correlation function employed to correlate the stored EGM's with the EGM template is the Kendall tau correlation function. As may be appreciated by those skilled in the art, other correlation functions may be employed instead without departing from the present inventions.

Figure 3:
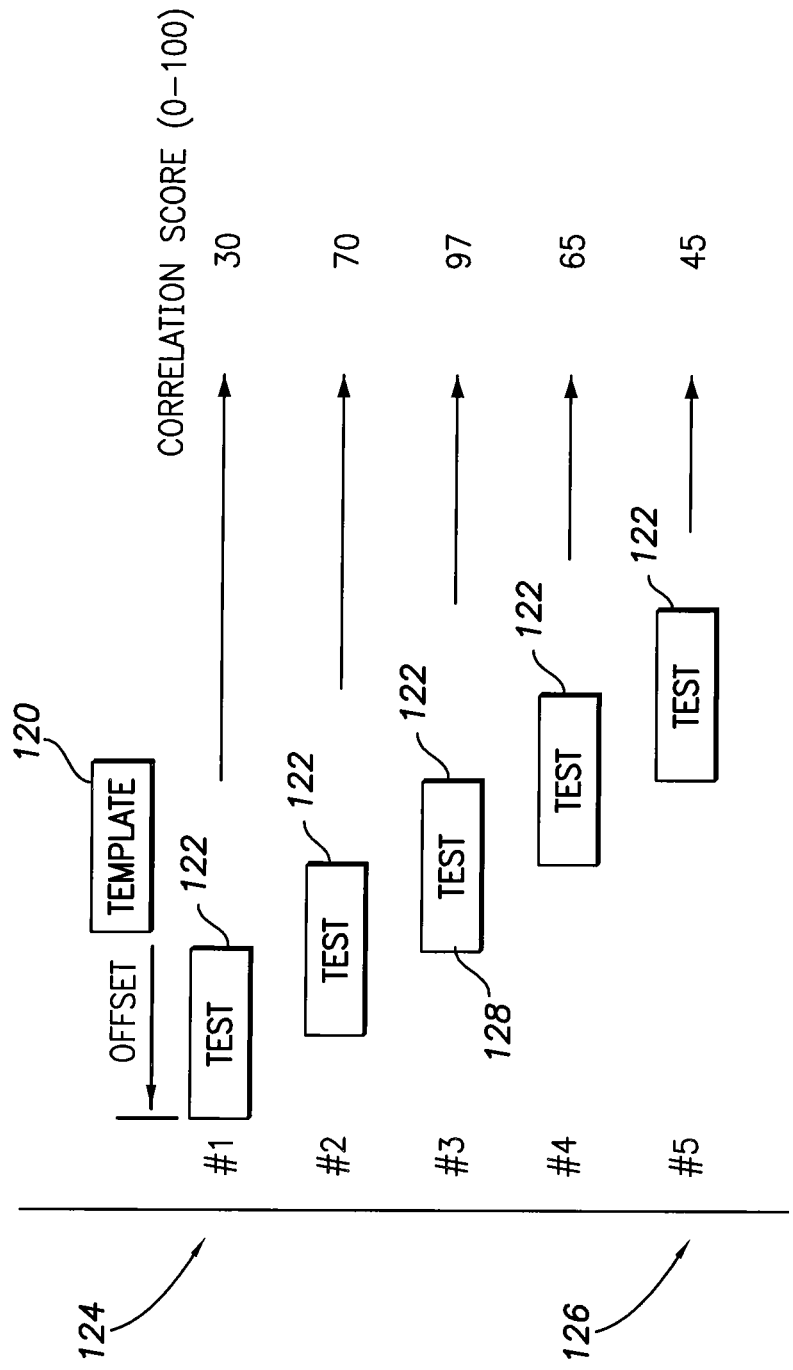
FIG. 3 is a graphical representation of a manner in which a stored electrogram (EGM) may be correlated with an EGM template in accordance with an embodiment of the invention to detect the time of occurrence of a cardiac event.

The forgoing may be better understood by making reference to FIG. 3. Here a template 120 and a recorded EGM 122 are being correlated fives times, with each correlation having a different offset between the template 120 and the recorded EGM. As previously mentioned, the template 120 and EGM 122 may actually be windows that capture the cardiac event of interest. The offset for the first correlation may be for example, a minus ninety milliseconds, with each correlation offset thereafter being incremented by forty-five milliseconds until a maximum offset of, for example, plus ninety milliseconds is reached (correlation 126). Each correlation results in a correlation score. When the maximum offset is reached, the offset with the highest correlation score is used to locate the start of the cardiac event. Here, for example, the offset with the highest correlation score corresponds to correlation 128. This correlation provides the best alignment of the template 120 and EGM 122 and enables the start point of the cardiac event of the EGM 122 to be located from the corresponding fiducial point on the template 120. The forgoing process is more particularly described below with respect to the flow chart of FIG. 4.

Figure 4:
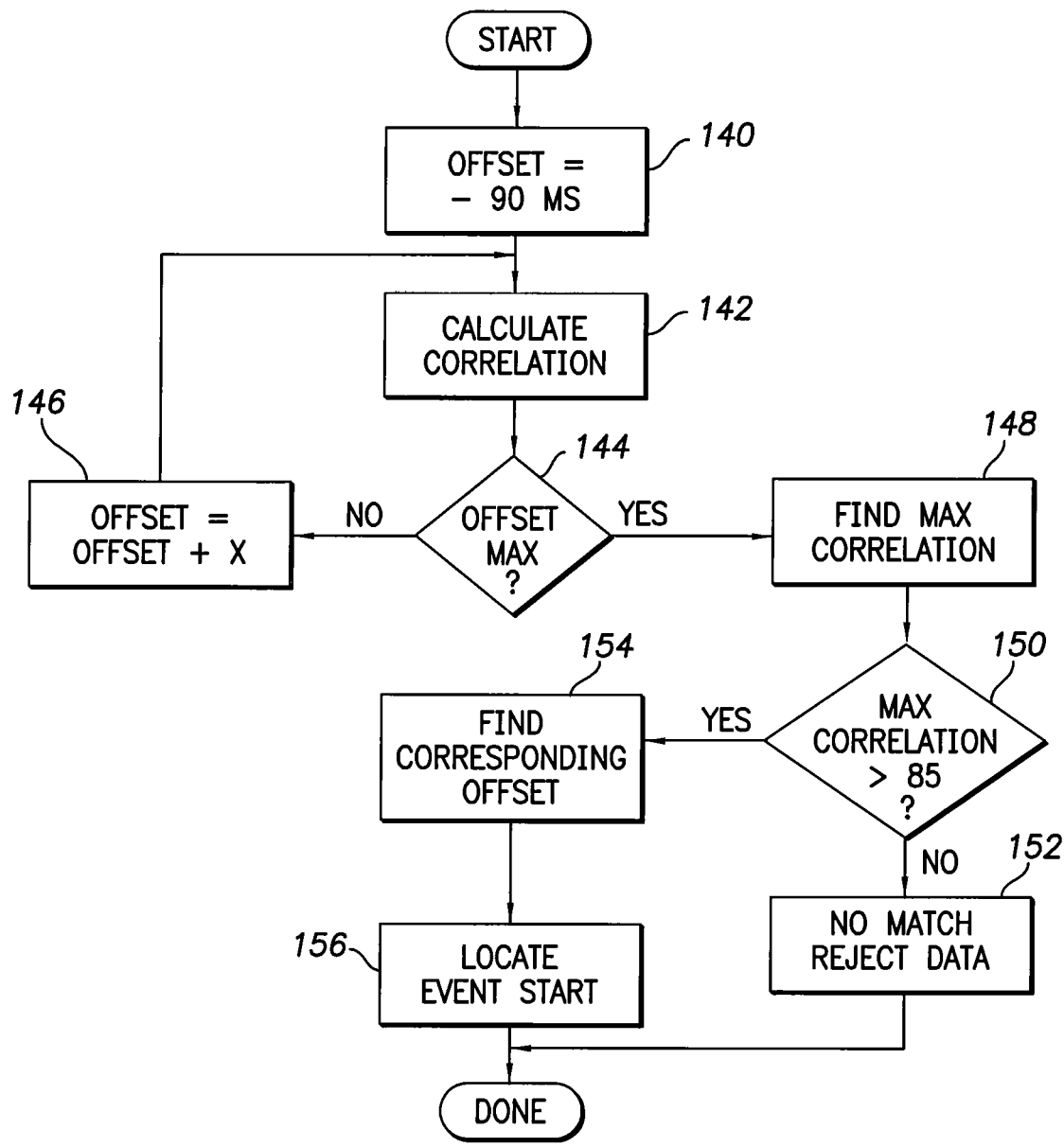
FIG. 4 is a flow chart describing an overview of the operation of an embodiment of the present invention.

In FIG. 4, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 4 initiates with activity block 140 wherein a first offset of minus ninety milliseconds is selected for the first correlation. The process then advances to activity block 142 where the correlation function is applied to the EGM 122 and the template 120. After the correlation is completed, the process advances to decision block 144 where it is determined if the maximum offset has been reached. If it has not, the process advances to activity block 146 where the offset is incremented by X milliseconds (here by forty-five milliseconds). Then the process returns to activity block for the running of another correlation.

The forgoing continues until in decision block 144 it is determined that the maximum offset has been reached. Then, in activity block 148 the maximum correlation score is found. The process then advances to decision block 150 to determine if the maximum correlation score is above a preset score such as, for example, eighty-five. If it is not, the process proceeds to activity block 152 to declare a data mismatch and reject the data as being too unreliable. The process would then complete.

However, if in decision block 150 it is determined that the maximum correlation score is above the preset score, the process advances to activity block 154 to find the offset that results in the maximum correlation score. That permits the time of occurrence or start of the cardiac event to be determined in activity block 156 by matching the EGM with the template and finding the point on the EGM that corresponds to the fiducial point on the template as previously described.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of detecting the time of occurrence of a cardiac event of a heart, the method comprising:
sensing electrical activity of the heart to generate an electrogram signal and identifying the cardiac event as an R-wave;
storing the electrogram signal;
after identifying the cardiac event as an R-wave, correlating the electrogram signal with an electrogram template, wherein the correlating comprises performing a plurality of different correlation calculations, where for each correlation calculation a different temporal offset between the electrogram signal and the electrogram template is selected; and
identifying the time of occurrence of the R-wave based upon the correlation calculations.

2. The method of claim 1, wherein the step of identifying the time of occurrence of the cardiac event based upon the correlation includes the steps of assigning a point on the electrogram template as a fiducial point and locating a point on the electrogram corresponding to the fiducial point on the electrogram template.

3. The method of claim 1, wherein the identifying step is performed if a highest correlation has a score above a preset score.

4. The method of claim 1, further comprising the steps of detecting the cardiac event with a set detection threshold and establishing a recording window spanning the detected cardiac event, wherein the correlating step includes retrospectively correlating the stored given cardiac event with the electrogram template over the recording window.

5. The method of claim 1, wherein the sensing step includes generating an electrogram signal and the storing step includes converting the electrogram signal to digital data for storage.

6. A system that detects the time of occurrence of a cardiac event of a heart, the system comprising:
a sensing circuit that senses electrical activity of the heart to generate an electrogram signal and that identifies the cardiac event as an R-wave;
a memory that stores the electrogram signal and an electrogram template; and
a processor that, after the R-wave is identified, correlates the electrogram signal with the electrogram template by performing a plurality of correlation calculations by temporally shifting the electrogram template relative to the electrogram signal to a different offset between the electrogram signal and the electrogram template for each said correlation calculation, and identifies the time of occurrence of the R-wave based upon the correlation calculations.

7. The system of claim 6, wherein the processor is programmed to assign a point on the electrogram template as a fiducial point corresponding to the time of occurrence of the cardiac event and to locate a point on the electrogram corresponding to the fiducial point on the electrogram template.

8. The system of claim 6, wherein the processor is programmed to identify the time of occurrence of the cardiac event based upon the correlation if a highest correlation has a score above a preset score.

9. The system of claim 6, further comprising a detector that detects the cardiac event with a set detection threshold and wherein processor is programmed to establish a recording window spanning the detected cardiac event and retrospectively correlate the recorded cardiac event with the electrogram template over the recording window.

10. The system of claim 6, further comprising an analog to digital converter that converts the electrogram signal to digital data for storage.

11. In an implantable cardiac device, a system that detects the time of occurrence of a cardiac event of a heart, the system comprising:
a sensing circuit that senses electrical activity of the heart to generate an electrogram signal and that identifies the cardiac event as an R-wave;
a memory that stores the electrogram signal and an electrogram template; and
a processor that, after the R-wave is identified, correlates the electrogram signal with the electrogram template by performing a plurality of correlation calculations by temporally shifting the electrogram template relative to the electrogram signal to a different offset between the electrogram signal and the electrogram template for each said correlation calculation, and identifies the time of occurrence of the R-wave based upon the correlation calculations.

12. The device of claim 11, wherein the processor is programmed to assign a point on the electrogram template as a fiducial point corresponding to the time of occurrence of the cardiac event and to locate a point on the electrogram corresponding to the fiducial point on the electrogram template.

13. The device of claim 11, wherein the processor is programmed to identify the time of occurrence of the cardiac event based upon the correlation if a highest correlation has a score above a preset score.

14. The device of claim 11, further comprising a detector that detects the cardiac event with a set detection threshold and wherein processor is programmed to establish a recording window spanning the detected cardiac event and retrospectively correlate the recorded cardiac event with the electrogram template over the recording window.

15. The device of claim 11, further comprising an analog to digital converter that converts the electrogram signal to digital data for storage.

* * * * *